Figure 1:
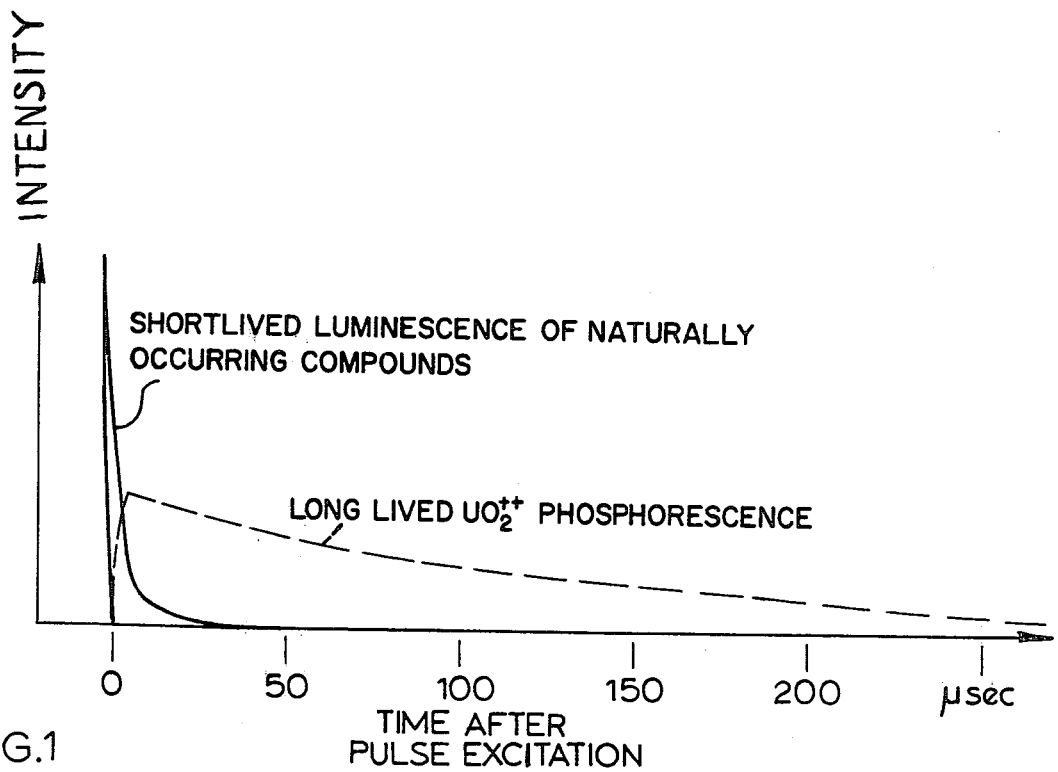

United States Patent [19]

Robbins et al.

[11] 4,198,568

[45] Apr. 15, 1980

[54] APPARATUS AND METHOD FOR URANIUM DETERMINATION

[75] Inventors: John C. Robbins, Alliston; John D. Kinrade, Ottawa, both of Canada

[73] Assignee: Scintrex Limited, Concord, Canada

[21] Appl. No.: 879,647

[22] Filed: Feb. 21, 1978

Related U.S. Application Data

[63] Continuation-in-part of Ser. No. 693,212, Jun. 4, 1976, abandoned.

[51] Int. Cl.² ............... G01N 21/38; G01V 5/00; G01J 1/58
[52] U.S. Cl. .................... 250/459; 250/255; 250/461 R
[58] Field of Search .......... 250/459, 461 R, 255, 250/304, 253, 365; 23/230 EP

[56] References Cited

FOREIGN PATENT DOCUMENTS 579864  7/1959  Canada ............... 23/230 EP

OTHER PUBLICATIONS

Vernon Hodge et al., "Semi-Quantitative Determination of Uranium, Plutonium and Americium in Sea Water," Analytical Chemistry, vol. 47, No. 11, Sep. 1975, pp. 1866–1868.

Primary Examiner—Alfred E. Smith
Assistant Examiner—Carolyn E. Fields
Attorney, Agent, or Firm—Fetherstonhaugh & Co.

[57] ABSTRACT

A method of detecting uranium compounds in an aqueous sample, containing uranium compounds that phosphoresce in response to ultraviolet light and other compounds which luminesce but have a shorter lifetime of phosphorescence than uranium compounds comprising the steps of increasing the phosphorescent characteristics of the uranium compounds and simultaneously diminishing the quenching efficiency of interfering ions in the sample by adding a polyphosphate compound and a buffer; projecting ultraviolet light into the sample; terminating said projection of ultraviolet light into the sample; measuring intensity of the decaying uranium phosphorescence at a time delay after the termination of the ultraviolet light, the time delay being longer than the time for luminescence due to materials other than uranium compounds possibly in the sample to substantially decay.

8 Claims, 2 Drawing Figures

APPARATUS AND METHOD FOR URANIUM DETERMINATION

This invention is a continuation-in-part to Application Ser. No. 693,212 filed on June 4, 1976, now abandoned.

This invention relates to a method for detecting uranium compounds in an aqueous solution that possibly contains a uranium compound that phosphoresces in response to ultraviolet light.

This specification uses the term "luminescence" as a general description of a light emitting process, usually caused by the excitation of a species by incident light. That emission which persists for a measurable period (e.g. some microseconds or longer) after the incident radiation has been terminated, is called phosphorescence. The term "fluorescence" applies to species whose emission ceases within a very short period (usually nanoseconds) after the incident radiation has been terminated.

It is not broadly new to use the luminescent characteristics of uranium compounds for the purpose of detecting a uranium compound in a sample. Uranium has a characteristic green luminescence which can be isolated by optical filters and its intensity measured with a photo detector, whose electrical output is considered to be an indication of the uranium concentration in the sample.

The known luminescent methods, as applied to uranium analysis, however, are very complex, slow and prone to contamination. For example, in accordance with the method commonly used, an aqueous sample thought to contain a uranium compound is first evaporated carefully to dryness and the residue fused at a high temperature with a carbonate-fluoride flux to produce a glass-like disc. The disc is then placed in an optical fluorimeter wherein it is illuminated by ultraviolet light to cause the uranium to luminesce and the luminescent intensity is measured during the excitation period.

With the method of this invention, it is possible to make a much more convenient and direct measurement on aqueous samples to detect the existence of uranium compounds in the samples. The measurements can be made "in the field" as well as in a laboratory.

In mineral exploration, it is often important to know the uranium content in natural waters, i.e. those waters which occur naturally as lakes and rivers, or ground waters. Typically, natural waters away from uranium bearing mineralization might contain 0.1 ppb uranium or less but waters draining or in contact with such mineralization might have values in the 1-100 ppb uranium range. The importance of the present invention to mineral exploration is readily apparent.

The use of the invention, however, is not restricted to mineral exploration. It can be used to advantage in any case where one wants to detect uranium compounds in an aqueous solution.

A method of detecting uranium compounds in an aqueous sample, containing uranium compounds that phosphoresce in response to ultraviolet light and other compounds which luminesce but have a shorter lifetime of phosphorescence than uranium compounds comprises the steps of increasing the phosphorescent characteristics of the uranium compounds and simultaneously diminishing the quenching efficiency of interfering ions in the sample by adding a polyphosphate compound and a buffer, projecting ultraviolet light into the sample, terminating said projection of ultraviolet light into the sample; measuring intensity of the decaying uranium phosphorescence at a time delay after the termination of the ultraviolet light, the time delay being longer than the time for luminescence due to materials other than uranium compounds possibly in the sample to substantially decay.

The invention will be clearly understood after reference to the following detailed specification read in conjunction with the drawings.

Figure 2:
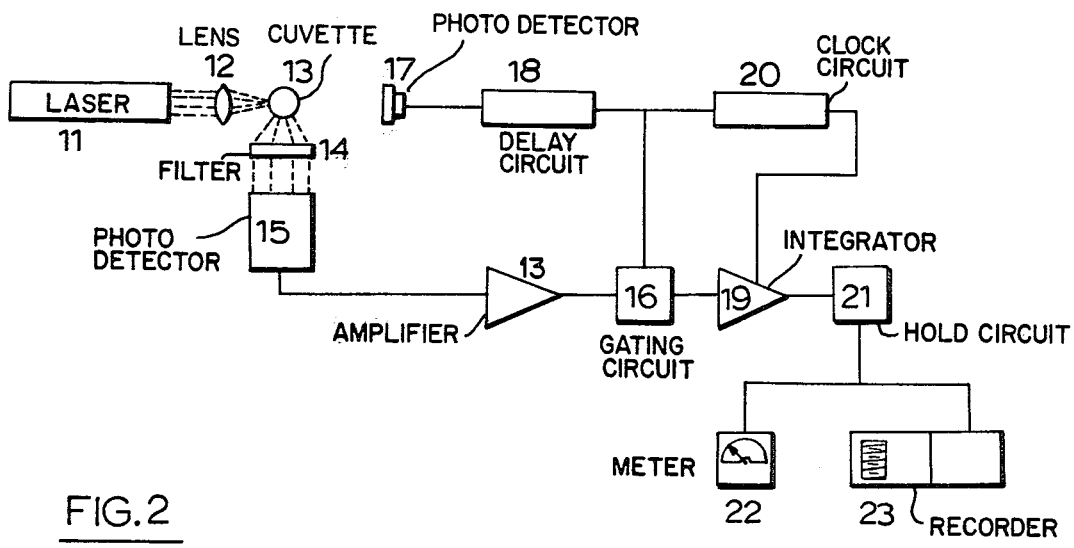

In the drawings:

FIG. 1 is a graph illustrating the decay of intensity of phosphorescence of hexavalent uranium and luminescence due to naturally occurring compounds in natural waters; and FIG. 2 is a block diagram of apparatus in accordance with this invention.

As indicated, this invention makes use of the fact that under excitation by ultraviolet light, uranium compounds phosphoresce with emission of a characteristic green light. It is believed that only hexavalent uranium, $U^{6+}$, present in the uranyl ion, $UO_2^{++}$ phosphoresce, the quadrivalent uranium ion being nonluminescent.

Uranium has an anomalously long phosphorescent decay time (half life of the order of 50 to 200 microseconds). It has been found that the luminescent half lives of most compounds which might commonly be found in association with uranium in its natural state are of the order of a microsecond or less. Thus, with this type of sample one can detect and analyse for uranium without concern for contaminating ions.

Indeed, a further objective of this invention is to provide means for supressing the interference or quenching effects of the contaminating ions.

As an example of the method, a short ultraviolet light pulse, between 5-10 nanoseconds long, was generated by a laser and directed at a number of aqueous samples, some of which contained a uranium compound that phosphoresces in response to ultraviolet light. FIG. 1 is a graph illustrating the lifetime of phosphorescence after termination of ultraviolet excitation for a uranyl compound, compared to other compounds that luminesce in natural waters.

From FIG. 1 it can be observed that the emission of the long-lived uranyl species may readily be distinguished from that of the short lived contaminants.

Measurement of the intensity of the "tail" due to the uranium phosphorescence is a measure of the presence and amount of the uranium compound in the sample. The intensity measurements are made by a suitable photo detector and electronic means. In the case of the sample tested in FIG. 1, if the measurements are made after luminescence due to materials other than uranium compounds have died down, (e.g. after 25 microseconds) then the measurement of intensity is substantially due to the phosphorescence of the uranium compound.

In the analysis of uranium by spectrofluorimetry wherein the luminescent yield of the uranyl species is measured during the excitation process there are many ions such as Ca, Mg and Fe which interfere with the measurement, i.e. by partially or wholly quenching the uranyl luminescence. The objectives of many of those trying to improve the methods have been to reduce these effects by prior separation of the contaminating ions and/or by enhancement of the luminescent yield through additives.

It has been found that the addition of buffered polyphosphate ions to an aqueous solution containing uranium compounds buffered to a pH in the region of 7 or 8, dramatically enhances the phosphorescent yield and in addition serves to mask interfering ions by forming polyphosphate complexes with them. By reason of the yield enhancement detection and analyses is easier and by reason of the masking the interfering ions are much less (about four times for iron) effective in quenching the uranyl phosphorescence.

The family of polyphosphates comprises anions containing oxygen, possibly hydrogen, and at least two phosphorous atoms (in oxidation level 5). Among the more common members of this family are, in the linear series, pyrophosphate, tripolyphosphate and tetraphosphate and in the cyclic series, trimetaphosphate, tetrametaphosphate and hexametaphosphate.

Whilst the optimum pH is about 7 it has been found that a useful result can be achieved with a broader range. Table I shows the relative effect on the phosphorescent yield of a uranyl ion bearing solution where the pH only of the solution was varied.

TABLE I

| pH | RELATIVE PHOSPHORESCENT YIELD |
|---|---|
| 9 | 71 |
| 8 | 100 |
| 7 | 100 |
| 6 | 79 |
| 5 | 54 |

Table II shows the phosphorescence enhancement factors of typical polyphosphates of a 2 ppb uranyl ion standard solution, normalized by the yield observed with no additive.

TABLE II

| ADDITIVE | FORMULA | NORMALIZED RELATIVE YIELD |
|---|---|---|
| Sodium pyrophosphate | $Na_4P_2O_7$ | 80 |
| Sodium tripolyphosphate | $Na_5P_3O_{10}$ | 44 |
| Sodium metaphosphate | $(NaPO_3)_{13}$ | 80 |
| Sodium trimetaphosphate | $Na_3P_3O_9$ | 40 |

Although sodium salts of the polyphosphate anions were used in the experiments described in this table the nature of the anion is not important and any convenient soluble salts of the polyphosphate anion would be effective.

This family of reagents is sensitive to acid and will decompose to simple monophosphates in highly acidic solutions particularly if the solutions are warmed much above 70° F. The monophosphate solution so generated is considerably less effective in stimulating the luminescent efficiency of the uranyl ion.

While there is a difference in the effect of the polyphosphates listed in Table II they are all suitable for the invention and all show substantial advantage over known methods of uranium detection.

In all cases the polyphosphate was added to the buffer in the ratio of about 1 to 10. Prior to the uranium analysis the polyphosphate-buffer solution is added to the sample in approximately a 1.0 to 10 ratio. Due to the viscosity of the reagent, care must be taken to ensure that the sample is stirred or otherwise agitated to obtain a homogeneous mixture.

In FIG. 2, a block diagram of a suggested apparatus for practising the invention is illustrated. A laser 11 generates a short but intense ultraviolet light pulse. In the embodiment illustrated, the laser is a nitrogen laser constructed after the design of Small et al which delivers a peak power of about 20 kilowatts at a wave length of 3371° Angstrom in a pulse that lasts about 10 nanoseconds. The pulse rate of the laser is 15 per second and it consumes about 5 watts of electrical power.

A lens 12 focuses the laser beam into a transparent cuvette 13 that contains an aqueous sample to be tested and a buffered polyphosphate additive, so that any uranium compound in the sample will phosphoresce in response to ultraviolet light. The resultant green phosphorescence of a uranium compound that might be in the sample is isolated by a filter 14 before irradiating the photocathode surface of the photodetector 15. The filter 14 is an optical thin-film filter.

The output of the photodetector 15 is amplified in amplifier 13 and fed to an electronic gating circuit 16. A second photodetector 17 monitors the incident laser beam and is used to trigger a delay circuit 18 that allows only that phosphorescence attributable to uranium to pass through the gate circuit by operating to permit passage only after a time delay within which luminescence due to materials other than uranium have dropped to a value at which they are insignificant. The delay period has been typically set at between 20-50 microseconds.

The resulting periodic signal is fed to an integrator 19 which is allowed to sum the intensity of the phosphorescence primarily due to uranium for 16 pulses and then give a readout of intensity. Following readout, it is reset by an electronic clock circuit 20 driven by the trigger circuit. Just prior to reset, a sample and hold circuit 21 samples the integrator and transfers the information to a meter 22 and recorder 23.

The time delay after the termination of the projection of the ultraviolet pulse into the sample, after which intensity measurement takes place, is capable of variation and quite feasibly might be as small as 5 microseconds. It should be sufficiently long after the termination of the pulse of light so that there will be no electrical noise interference, such as is commonly present from a pulsed laser. It also must be a duration longer than the lifetime of luminescence of the other compounds in the material that luminesce. Sources of ultraviolet light other than a laser beam can be used although the highly directional properties of such a beam are very desirable. For example, a pulsed Zenon arc lamp might be used, which has an output ranging from the ultraviolet to the infrared and would thus require considerable spectral filtering to avoid light scattering. The laser is to be preferred because it has output at only one wave length (3371° A) although it is not thought of as the only possible source of ultraviolet light that can irradiate the sample. The laser repetition rate in the example given or 15 pulses per second was conveniently locked to a subharmonic of the frequency of the power supply, the frequency of this being 60 cycles per second. If the laser repetition rate was increased, it would require more power to provide the greater number of pulses per second. By increasing the pulse frequency, it would, of course, improve the detection limit for a given period of phosphorescent intensity integration.

In a typical uranium measurement, the nitrogen laser is set to deliver about 20-30 kilowatts peak power in a beam focussed onto a small cuvette into which some 5-10 ml of the sample, including reagent, is placed. The phosphorescence of the sample is monitored by two photomultipliers. In front of one of these a filter with a spectral response optimized for uranium phosphorescence (4900°-5200° A) is placed; in front of the other, the reference detector, a filter with peak transmission at wavelengths 4500°–4700° A is placed. With such a dual detector system and suitable electronics recorder responses of the order of 10 V per ppb uranium are obtained. Detector limits of 0.03 ppb uranium have been achieved. The effect of interfering ions has been checked to verify the efficacy of the buffer-polyphosphate additive. It has been found that useful uranium analyses can be made even in the presence of as much as 10–100 ppm quantities of $Cl^-$ and $CO_3^{--}$ and 10–50 ppm levels of Fe and $Mn^{++}$ which are effectively masked by the present system. Without the added reagent, such quantities totally quench the uranium phosphorescence signal.

What we claim as our invention is:

1. A method of detecting uranium compounds in an aqueous sample, containing uranium compounds that phosphoresce in response to ultraviolet light and other compounds which luminesce but have a shorter lifetime of phosphorescence than uranium compounds comprising the steps of:
   (a) increasing the phosphorescent characteristics of the uranium compounds and simultaneously diminishing the quenching efficiency of interfering ions in the sample by adding a polyphosphate compound and a buffer;
   (b) projecting ultraviolet light into the sample;
   (c) terminating said projection of ultraviolet light into the sample;
   (d) measuring intensity of the decaying uranium phosphorescence at a time delay after the termination of the ultraviolet light, the time delay being longer than the time for luminescence due to materials other than uranium compounds possibly in the sample to substantially decay.

2. A method of detecting uranium compounds in an aqueous sample containing uranium compounds that phosphoresce in response to ultraviolet light and other compounds which luminesce but have a shorter lifetime of phosphorescence than uranium compounds as claimed in claim 1 wherein said sample is buffered to maintain a pH of between 5–10.

3. A method of detecting uranium compounds in an aqueous sample containing uranium compounds that phosphoresce in response to ultraviolet light and other compounds which luminesce but have a shorter lifetime of phosphorescence than uranium compounds as claimed in claim 1 wherein said sample is buffered to maintain a pH of between 6–8.

4. A method of detecting uranium compounds in an aqueous sample containing uranium compounds that phosphoresce in response to ultraviolet light and other compounds which luminesce but have a shorter lifetime of phosphorescence than uranium compounds as claimed in claim 1 wherein said sample is buffered to maintain a pH of about 7.

5. A method of detecting uranium compounds in an aqueous sample containing uranium compounds that phosphoresce in response to ultraviolet light and other compounds which luminesce but have a shorter lifetime of phosphorescence than uranium compounds as claimed in claim 1 wherein said polyphosphate compound is a polyphosphate compound taken from the group pyrophosphate, tripolyphosphate, tetraphosphate, trimetaphosphate, tetrametaphosphate and hexametaphosphate.

6. A method of detecting uranium compounds in an aqueous sample containing uranium compounds that phosphoresce in response to ultraviolet light and other compounds which luminesce but have a shorter lifetime of phosphorescence than uranium compounds as claimed in claim 2 wherein said polyphosphate compounds is a polyphosphate compound taken from the group pyrophosphate, tripolyphosphate, tetraphosphate, trimetaphosphate, tetrametaphosphate and hexametaphosphate.

7. A method of detecting uranium compounds in an aqueous sample containing uranium compounds that phosphoresce in response to ultraviolet light and other compounds which luminesce but have a shorter lifetime of phosphorescence than uranium compounds as claimed in claim 3 wherein said polyphosphate compounds is a polyphosphate compound taken from the group pyrophosphate, tripolyphosphate, tetraphosphate, trimetaphosphate, tetrametaphosphate, and hexametaphosphate.

8. A method of detecting uranium compounds in an aqueous sample containing uranium compounds that phosphoresce in response to ultraviolet light and other compounds which luminesce but have a shorter lifetime of phosphorescence than uranium compounds as claimed in claim 4 wherein said polyphosphate compounds is a polyphosphate compound taken from the group pyrophosphate, tripolyphosphate, tetraphosphate, trimetaphosphate, tetrametaphosphate and hexametaphosphate.

* * * * *